United States Patent
Muller

(10) Patent No.: US 7,025,759 B2
(45) Date of Patent: Apr. 11, 2006

(54) STEERABLE CATHETER

(75) Inventor: Charles Muller, Millington, NJ (US)

(73) Assignee: EBI, L.P., Parsippany, NJ (US)

(*) Notice: Subject to any disclaimer, the term of this patent is extended or adjusted under 35 U.S.C. 154(b) by 165 days.

(21) Appl. No.: 10/358,021

(22) Filed: Feb. 4, 2003

(65) Prior Publication Data

US 2003/0149422 A1 Aug. 7, 2003

Related U.S. Application Data

(60) Provisional application No. 60/354,158, filed on Feb. 4, 2002.

(51) Int. Cl.
*A61M 25/01* (2006.01)
*A61M 25/02* (2006.01)
*A61M 25/04* (2006.01)
*A61M 25/06* (2006.01)
*A61M 25/08* (2006.01)

(52) U.S. Cl. .................. 604/528; 604/95.04; 604/510; 600/114; 600/146

(58) Field of Classification Search ............... 604/510, 604/95.01, 95.04, 163.13, 528; 600/434, 600/585, 114, 146

See application file for complete search history.

(56) References Cited

U.S. PATENT DOCUMENTS

| | | | | |
|---|---|---|---|---|
| 4,067,371 A | * | 1/1978 | Stencel | 411/107 |
| 5,224,939 A | * | 7/1993 | Holman et al. | 604/528 |
| 6,126,633 A | * | 10/2000 | Kaji et al. | 604/95.04 |
| 6,213,974 B1 | * | 4/2001 | Smith et al. | 604/95.01 |
| 6,648,875 B1 | * | 11/2003 | Simpson et al. | 604/528 |
| 6,652,506 B1 | * | 11/2003 | Bowe et al. | 604/523 |

* cited by examiner

*Primary Examiner*—Nicholas D. Lucchesi
*Assistant Examiner*—Catherine S. Williams
(74) *Attorney, Agent, or Firm*—Harness, Dickey & Pierce, P.L.C.

(57) ABSTRACT

A steerable catheter includes a housing, an elongated tube, a steering member and a retention mechanism. The elongated tube extends from the housing. The steering member is movably attached to the housing and is interconnected to a distal tip of the elongated tube such that movement of the steering member causes a corresponding angular movement of the distal tip. The retention mechanism is carried by at least one of the steering member and the housing. The retention mechanism is operative in the first mode to provide smooth movement of the steering member relative to the housing and further operative in a second mode to provide ratcheted movement of the steering member relative to the housing.

7 Claims, 4 Drawing Sheets

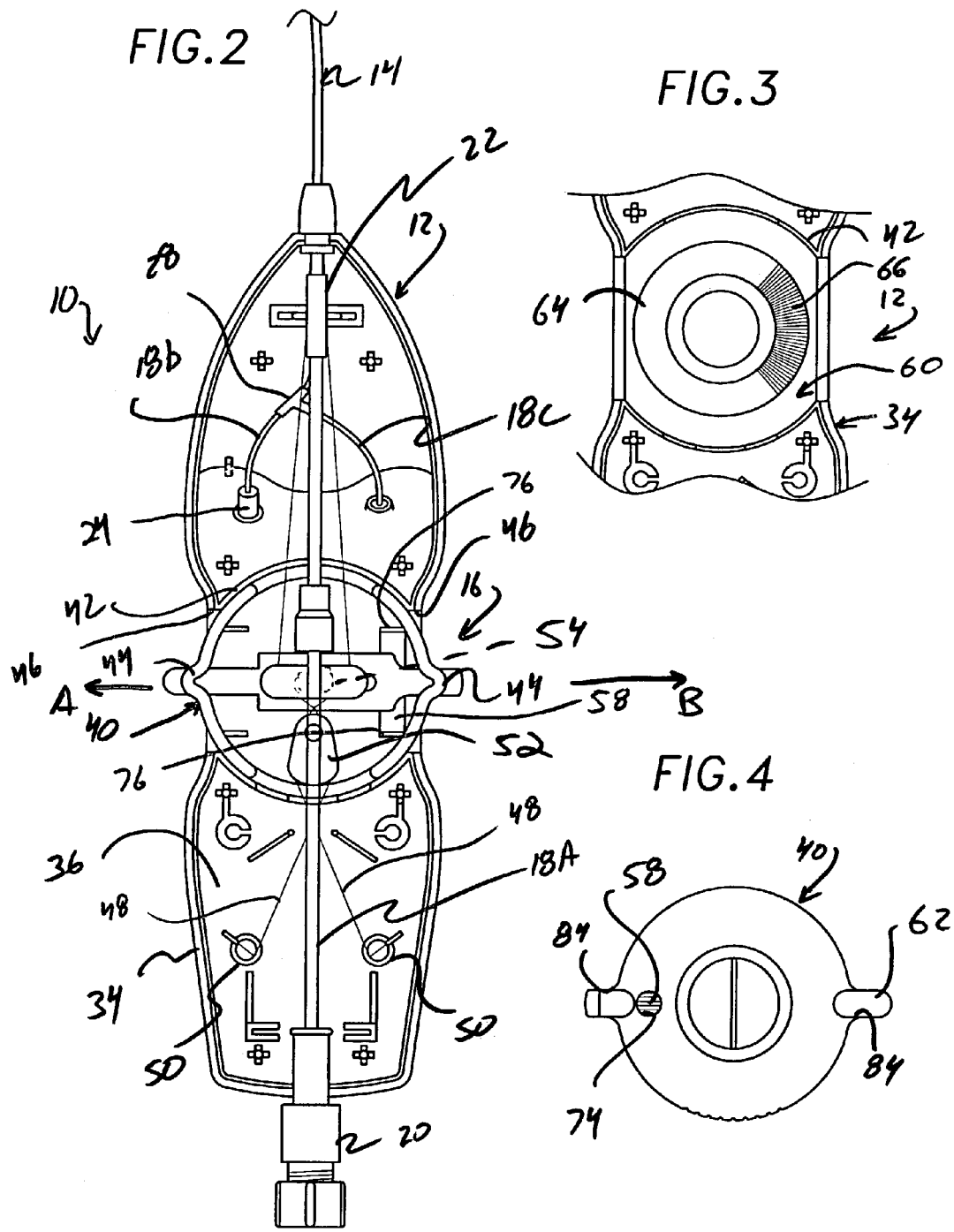

STEERABLE CATHETER

CROSS-REFERENCE TO RELATED APPLICATION

This application claims priority to a provisional patent application which has been assigned U.S. Ser. No. 60/354,158, filed Feb. 4, 2002.

FIELD OF THE INVENTION

The present invention generally relates to medical catheters and more specifically relates to a steerable catheter having a position retention mechanism. While not limited thereto, the present invention more particularly relates to a position retention mechanism for a steerable catheter that provides a first mode of operation for smooth steering movement of a manually controlled guide element and a second mode of operation for ratcheted steering movement of the manually controlled guide element.

BACKGROUND OF THE INVENTION

Various surgical procedures employ a catheter for the introduction of surgical tools, fluids or other materials into the body. For example, catheters are used for the introduction of items including but not limited to radiographic contrast materials, angioplasty balloons, fiber optic scopes, laser lights, and cutting instruments into the vessels, cavities, or tissues of a human body.

It is known to provide a catheter with an arrangement for steering through body vessels or cavities. For example, U.S. Pat. No. 5,437,636 to Snoke et al. discloses a catheter for use in body vessels or cavities having a housing and an elongated tube. The elongated tube has one end connected to the housing, extends outwardly therefrom and is formed of material of such a stiffness so as to normally maintain the elongated tube in a straight condition in the absence of an external force. An outer end portion of the elongated tube is relatively flexible. Guide wires are connected to the housing and extend outwardly through the elongated tube. The outer ends of the guide wires are connected to the flexible outer end portion of the elongated tube. A guide wire control mechanism is carried by the housing and cooperates with the guide wires for manually controlling the angular attitude of the flexible outer end portion of the elongated tube to thereby effectively "steer" the catheter. U.S. Pat. No. 5,473,636 is incorporated by reference as if fully set forth herein.

It is also known in the pertinent art to provide a steerable catheter with a locking mechanism for arresting the relative position of an elongated tube. In a conventional manner, a steering wheel is manually used to articulate the elongated tube for navigation through a vessel, cavity, or tissue of a patient. Manually releasing the steering wheel returns the elongated tube to its straight condition. At certain points during any particular surgical procedure, it may be desired to arrest the relative orientation of the elongated tube. At such time, the conventional locking mechanism is activated and movement of the steering wheel relative to the remainder of the catheter is effectively precluded.

While known locking mechanisms for steerable catheters have proven to be acceptable for their intended applications, they are all associated with limitations. Principally insofar as the present invention is concerned, maintaining a relative orientation of the elongated tube conventionally requires a secondary operation to activate a locking mechanism. Accordingly, it remains a need in the pertinent art to provide a retention mechanism for a steerable catheter that permits a surgeon to easily toggle between a first mode in which a steering wheel freely rotates and a second mode in which motion of the steering wheel is ratcheted.

SUMMARY OF THE INVENTION

It is a general object of the present invention to overcome the limitations of the prior art, including but not limited to those discussed above, by providing a steerable catheter operable in a first mode for smooth steering movement of a tip of an elongated tube and a second mode for ratcheted steering movement of the tip of the elongated tube.

It is a more particular object of the present invention to provide a steerable catheter having an arm slidably disposed through a steering wheel for influencing a locking tab into engagement with grooves carried by a housing of the catheter.

It is another more particular object of the present invention to provide a steerable catheter having an arm slidably disposed through a steering wheel for actuating a locking element into engagement with grooves disposed radially about the circumference of the steering wheel.

It is yet another particular object of the present invention to provide a steerable catheter having a locking ring with grooves incorporated on an inner diameter for engaging cooperating grooves on a steering wheel and a lever operated cam that cooperates with a split in the locking ring to influence the locking ring to a circumferentially expanded position.

In one form, the present invention provides a steerable catheter including a housing, an elongated tube, a steering member and a retention mechanism. The elongated tube extends from the housing. The steering member is movably attached to the housing and is interconnected to a distal tip of the elongated tube such that movement of the steering member causes a corresponding angular movement of the distal tip. The retention mechanism is carried by at least one of the steering member and the housing. The retention mechanism is operative in the first mode to provide smooth movement of the steering member relative to the housing and further operative in a second mode to provide ratcheted movement of the steering member relative to the housing.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 2 is a rear view of the steerable catheter of the first preferred embodiment of the present invention shown with a bottom clam shell half of the housing removed for purposes of illustration.

FIG. 3 is a rear view of a central portion of the upper clam shell half of the housing of the steerable catheter of the first preferred embodiment of the present invention shown operatively associated with a locking plate.

FIG. 4 is a front view of a guide wheel of the steerable catheter of the first preferred embodiment of the present invention shown with a portion of a locking tab extending through an aperture therein.

DETAILED DESCRIPTION OF THE PREFERRED EMBODIMENTS

The following description of the preferred embodiment(s) is merely exemplary in nature and is in no way intended to limit the invention, its application, or uses.

With reference to FIGS. 1–7, a steerable catheter constructed in accordance with the teachings of a first preferred embodiment of the present invention is illustrated. The steerable catheter is generally identified at reference element 10 and is illustrated to generally include a housing 12 and an elongated tube 14. The elongated tube extends from the housing 12 for the introduction of items including but not limited to radiographic contrast materials, angioplasty balloons, fiber optic scopes, laser lights, and cutting instruments into the vessels, cavities, or tissues of a human body. As will become fully understood below, the present invention primarily relates to a retention mechanism or arrangement 16 that provides for a first mode of catheter operation in which the elongated tube 14 is smoothly moved through a range of motion and a second mode of catheter operation in which the elongated tube 14 is ratcheted through its range of motion.

Figure 1:
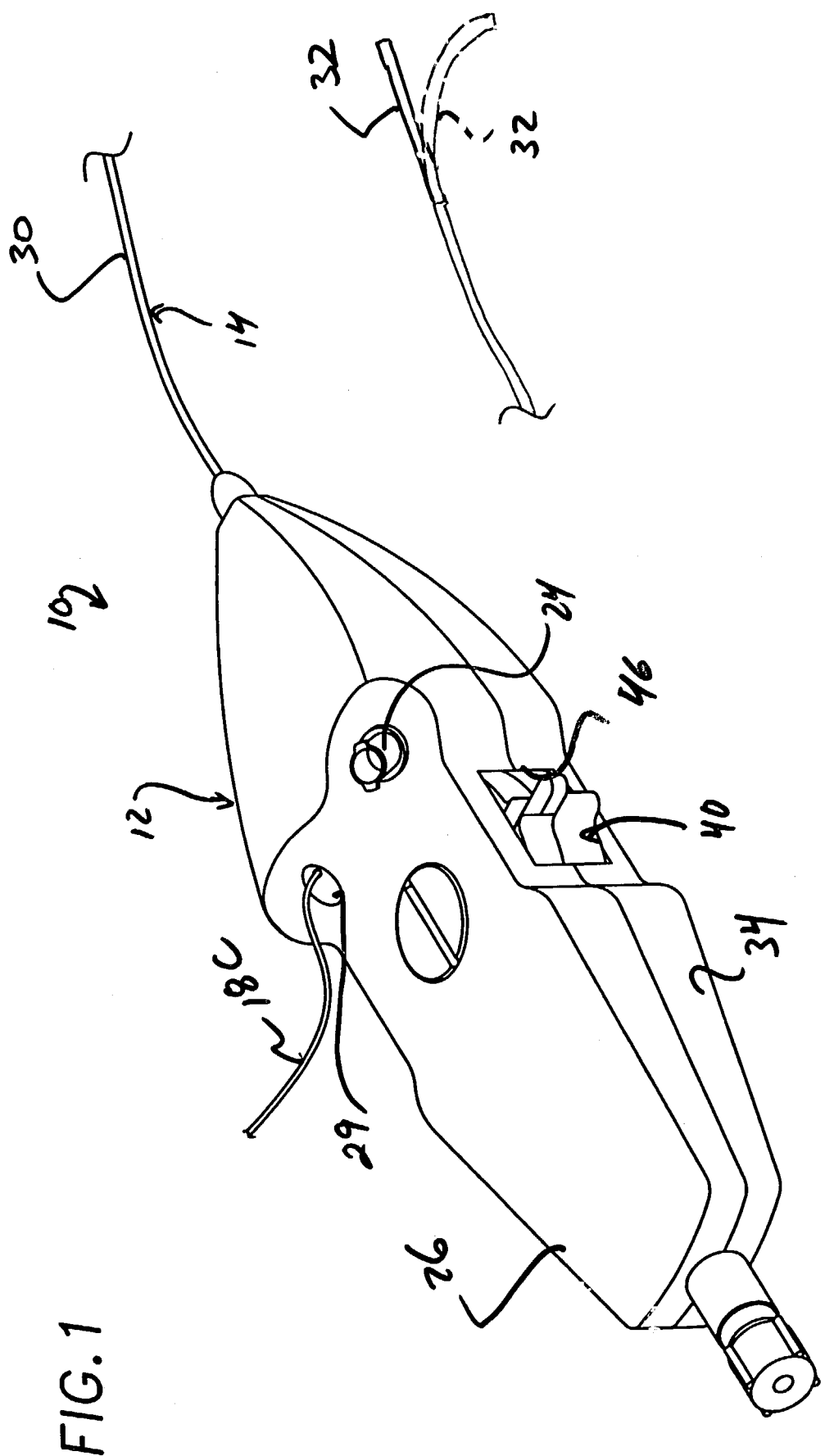
FIG. 1 is a front and side perspective view of a steerable catheter constructed in accordance with the teachings of a first preferred embodiment of the present invention.

Prior to addressing the construction and operation of the retention mechanism 16 of the first preferred embodiment of the present invention in detail, an understanding of the remainder of the catheter 10 is warranted. With particular reference to FIGS. 1 and 2, the catheter 10 is illustrated to include a plurality of tubes 18A–18C in communication with the elongated tube 14. A first of the tubes 18A has an input 20 adjacent a proximal end of the housing 12 and is coupled to the elongated tube 14 at a junction block 22. A second of the tubes 18B is coupled to the junction block 22 at one end and terminates at an input port 24 at its other end. The input port 24 extends through an upper clam shell half 26 of the housing 16. A third of the tubes 18C is in communication with the elongated tube 14 through the second tube 18B. In this regard, one end of the third tube 18C communicates with the second tube 18B through a T-connector 28. The third tube 18C extends through an aperture 29 in the upper clam shell half 26 and at its other end terminates at an input port (not shown). Insofar as the present invention is concerned, the tubes of the plurality of tubes 18A–18C are conventional in construction.

The elongated tube 14 includes a main portion 30 and a tip 32. The main portion 30 of the elongated tube 14 is constructed of a material having a stiffness that maintains the main portion 30 in a substantially straight condition in the absence of an external force. The tip 32 is constructed of a material which is generally more flexible than the main portion 30.

In addition to the upper clam shell half 26, the housing 12 includes a bottom or lower clam shell half 34. The clam shell halves 26 and 34 cooperate to define an inner cavity 36 and rotatably support a steering member 40. In the embodiment illustrated, the steering member is a circular guide wheel 40 and the lower clam shell half 34 is formed to include a partially circular flange 42 sized to receive the guide wheel 40. The guide wheel 40 includes a pair of radially extending tips 44 which extend through lateral openings 46 provided in the housing 12. The tips 44 facilitate manual grasping of the guide wheel 40 and cooperate with the housing 12 to limit the range of guide wheel rotation.

In a manner to be addressed, the guide wheel 40 cooperates with a pair of guide wires 48 to selectively articulate the tip 32 of the elongated tube 14 through its range of motion. It will be understood that the range of motion is within a plane perpendicular to an axis about which the guide wheel 40 rotates. The guide wheel 40 is shown in FIG. 2 in a neutral position such that the tip 32 of the elongated tube 14 is aligned generally coaxially with the main portion 30. The guide wheel 40 is rotatable from the neutral position in both clockwise and counterclockwise directions to facilitate a desired angular attitude of the tip 32. In the embodiment illustrated, the guide wheel 40 is rotatable through approximately 30° from the neutral portion in both clockwise and counterclockwise directions. Articulation of the tip 32 when the guide wheel 40 is rotated in a clockwise direction is shown in FIG. 1 in broken lines.

In a conventional manner, each of the guide wires 48 includes a first end anchored to a post 50 and a second end (not specifically shown) which is secured to a distal end of the tip 32. It will be understood that the particular manner of attachment of the guide wires 48 to the distal end of the tip 32 is beyond the scope of the present invention. However, one suitable manner known in the art is described in U.S. Pat. No. 6,030,360 which was incorporated by reference above.

The guide wires 48 pass by a camming member 52 carried by the guide wheel 40, around an opposite side of a center post 54 of the guide wheel 40, and through the main portion 30 of the elongated tube 14. In this fashion, the guide wire 48 secured to a right one of the posts 50 is secured to a right side of the tip 32 and the guide wire 48 secured to a left one of the posts 50 is secured to a left side of the tip 32. When the guide wheel 40 is rotated in a clockwise direction, the guide wire 48 secured to the right side of the tip 32 is pulled through the main portion 30 and the tip 32 bends to the right.

Articulation of the tip 32 to the left is similarly effectuated through counterclockwise rotation of the guide wheel 40.

With continued reference to FIGS. 1 and 2 and additional reference to FIGS. 3 through 7, the retention mechanism 16 of the first preferred embodiment of the present invention will be further described. The retention mechanism 16 is illustrated to generally include a locking tab 58, a locking plate 60 and an actuation member 62. The locking plate 60 is press fit into the opening of the clam shell half 34 of the housing 12 defined by the circular flange 42 and includes an upwardly extending portion 64 having a generally toroidal shape. The upwardly extending portion 64 is centered on the post 54 and includes at least a portion having a plurality of grooves or teeth 66. As will become apparent below, the plurality of teeth 66 are adapted to cooperate with a plurality of grooves or teeth 68 carried by the locking tab 58. In the embodiment illustrated, the plurality of teeth 66 are formed on the locking plate 60. Alternatively, the plurality of teeth 66 may be integrally formed directly with the housing 12.

Figure 5:
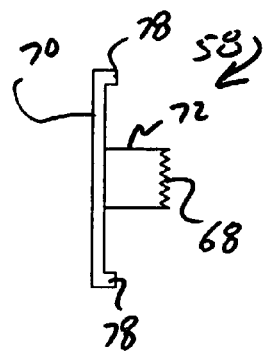
FIG. 5 is a side view of the locking tab of the steerable catheter of the first preferred embodiment of the present invention.

As shown particularly in the side view of FIG. 5, the locking tab 58 includes a planar portion 70 and a generally cylindrical post 72 which extends from the planar portion 70. The generally cylindrical post 72 extends through an aperture 74 in the guide wheel 40 as shown in FIG. 4. To prevent rotation of the locking tab 58 relative to the guide wheel 40, the planar portion 70 is positioned between a pair of flange elements 76 on the back surface of the guide wheel 40. The planar portion 70 is spaced from a rear surface of the guide wheel 40 by a pair of stand-off segments 78. The locking tab 58 is preferably constructed of a resilient plastic material. As such, the stand-off segments 78 normally provide a space between the pluralities of teeth 66 and 68. In a manner to be discussed below, the planar portion 70 can be biased such that the pluralities of teeth 66 and 68 engage.

Figure 6:
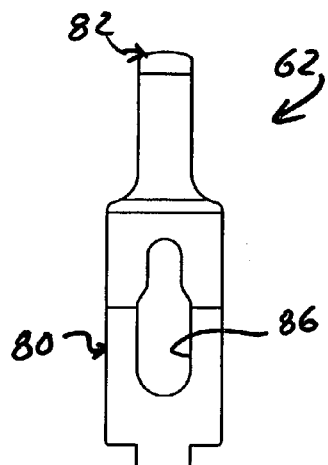
FIG. 6 is a front view of an actuation member of the steerable catheter of the first preferred embodiment of the present invention.
Figure 7:
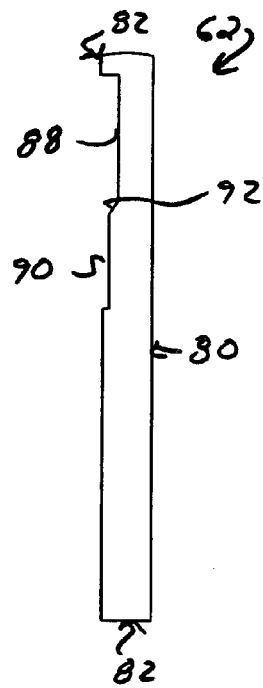
FIG. 7 is a side view of the actuation member of FIG. 6.
Figure 8:
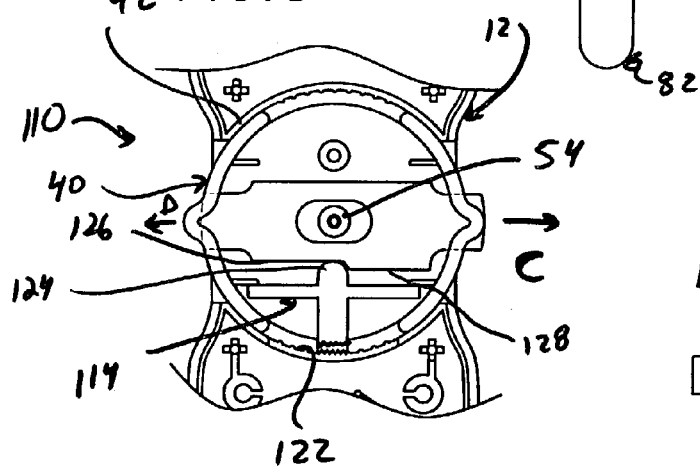
FIG. 8 is a view similar to FIG. 3 illustrating a partial rear view of a central portion of the front portion of the housing of the steerable catheter of a second preferred embodiment of the present invention.
Figure 9:
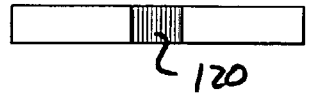
FIG. 9 is a side view of a locking element of the steerable catheter of the second preferred embodiment of the present invention.
Figure 10:
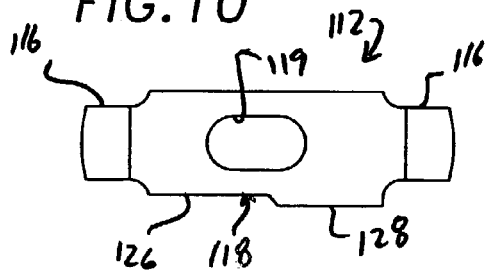
FIG. 10 is a front view of an actuation member of the steerable catheter of the second preferred embodiment of the present invention.
Figure 11:
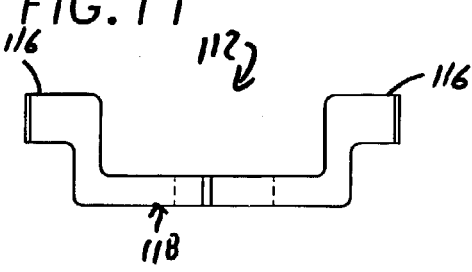
FIG. 11 is a side view of the actuation member of FIG. 10.

With particular reference to FIGS. 6 and 7, the actuation member 62 is shown to include a central portion 80 and a pair of ends 82. The ends 82 extend from openings 84 (as shown in FIG. 4) provided in the radially opposite sides of the guide wheel 40. The post 54 of the guide wheel 40 is received within an elongated opening 86 of the central portion 80 which thereby permits translation of the actuation member 62 along its long axis. The central portion 80 includes a stepped surface with a first or lower segment 88 and a second or raised segment 90 interconnected by a ramp 92. In the first mode, the actuation member 62 is translated in the direction of arrow A (see FIG. 2) and the planar portion 70 of the locking tab 58 is adjacent the lower segment 88. In this position, the standoff segments 78 of the locking tab 58 normally maintain a space between the pluralities of locking teeth 66 and 68 and smooth movement of the guide wheel 40 is permitted for steering the distal end of the tip 32. In a second mode of operation, the actuation member 62 is translated in the direction of arrow B (see FIG. 2) and the planar portion 70 of the locking tab 58 is adjacent the upper segment 90 of the actuation member 62. In this position, the actuation member 62 forces the pluralities of teeth 66 and 68 into engagement and movement of the guide wheel 40 relative to the housing 12 is ratcheted.

With reference to FIGS. 8 through 11, a steerable catheter constructed in accordance with a second preferred embodiment of the present invention is illustrated and generally identified at reference element 110. Similar to the steering catheter 10 of the first preferred embodiment of the present invention, the steering catheter 110 is operated in a first mode to provide smooth movement of a guide wheel 40 and a second mode to provide ratcheted movement of the guide wheel 40. Due to the similarities between the first and second preferred embodiments of the present invention, like reference elements have been used in the drawings to identified similar components.

The steerable catheter is illustrated to generally include an actuation member 112 and a locking element 114. Similar to the actuation member 62 of the first preferred embodiment, the actuation member 112 includes a pair of ends 116 and a central portion 118. The central portion 118 is stepped from the ends 116 and defines an elongated aperture 119 for receiving the post 54. The actuation member 112 is movable between first and second positions to effect the first and second modes of operation, respectively, in a manner substantially identical to the first preferred embodiment of the present invention.

The locking element 114 defines a first plurality of locking grooves or teeth 120 that cooperate with a second plurality of locking grooves or teeth 122 defined by the partially cylindrical flange 42 of the housing 12. When the actuation member 112 is translated in the direction of arrow C, a contact portion 124 of the locking element 114 is adjacent a first portion 126 of the central portion 18 and the plurality of teeth 120 of the locking element 14 are spaced from the plurality of teeth 122 of the housing 12. In this first mode of operation, smooth movement of the guide wheel 40 is permitted. When the actuation member 112 is translated in the direction of arrow D, the contact portion 124 of the locking element 114 is positioned adjacent a second portion 128 of the central portion 118 causing the pluralities of teeth 120 and 122 to engage. In this second mode of operation, movement of the guide wheel 40 relative to the housing 12 is ratcheted.

Figure 12:
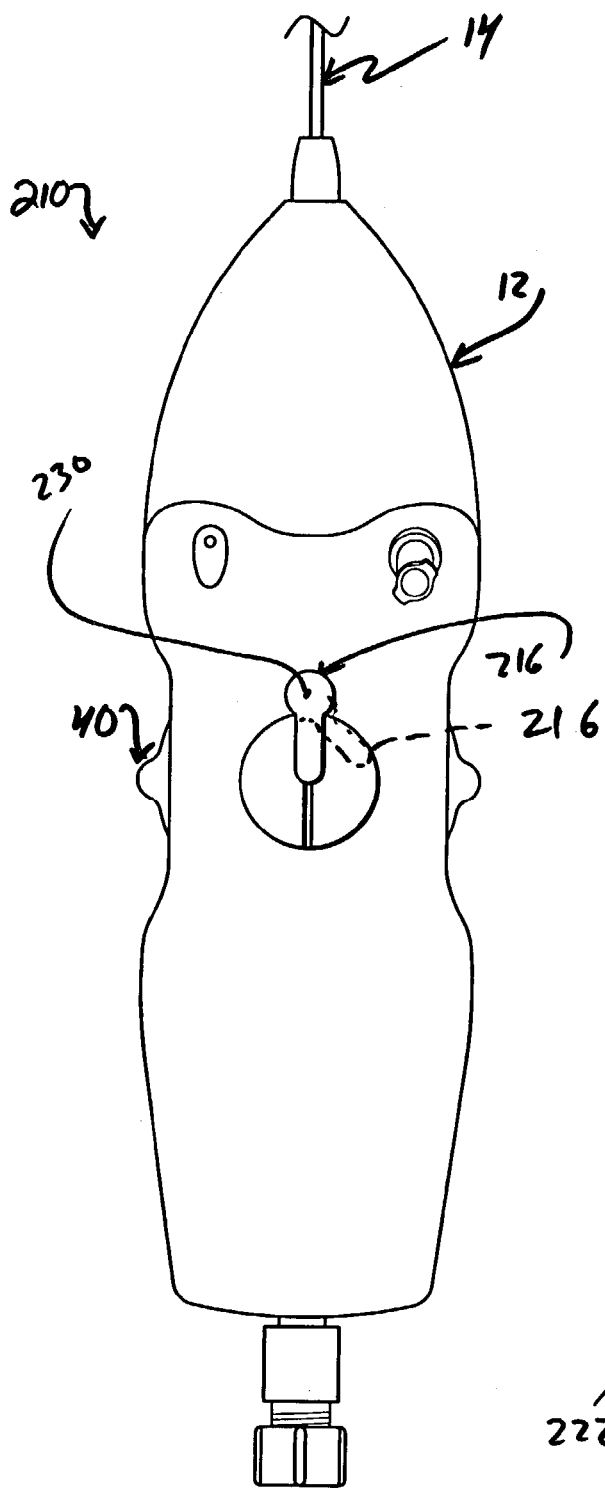
FIG. 12 is a front view of a steerable catheter constructed in accordance with the teachings of a third preferred embodiment of the present invention.
Figure 13:
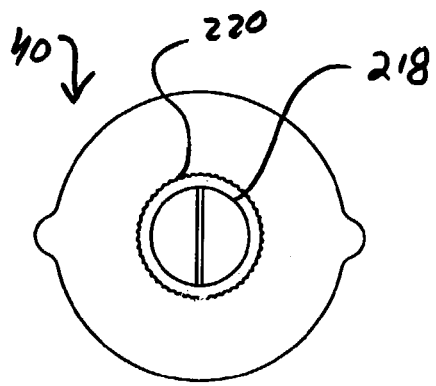
FIG. 13 is a view similar to FIG. 4, but illustrating the guide wheel of the steerable catheter according to the third preferred embodiment of the present invention.
Figure 14:
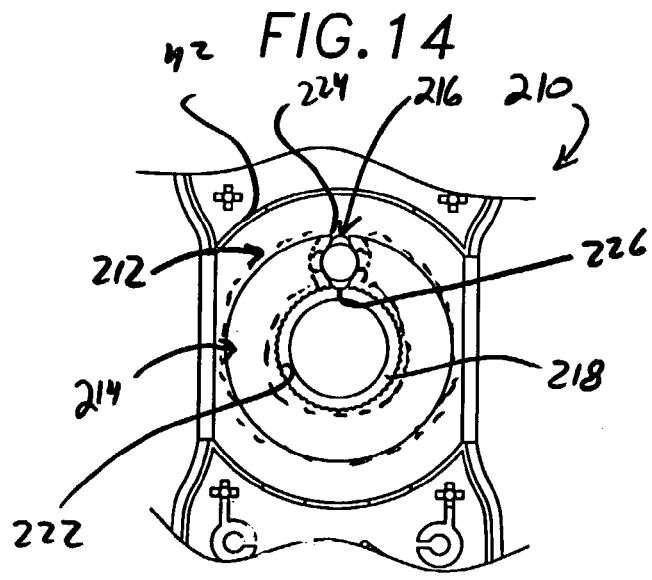
FIG. 14 is a view similar to FIG. 3, but illustrating the steerable catheter according to the third preferred embodiment of the present invention to include a split ring which cooperates with a stem of a manually operated lever to selectively alternate between the ratcheted and smooth movement.

With reference now to FIGS. 12 through 14, a steerable catheter constructed in accordance with a third preferred embodiment of the present invention is illustrated and generally identified at reference element 210. Again, the steerable catheter 210 of the third preferred embodiment of the present invention shares features with the steerable catheter 10 of the first preferred embodiment of the present invention. For this reason, like reference numerals have been used in the drawings to identify substantially identical components. The steerable catheter 210 principally differs from the steerable catheter 10 by providing a retention mechanism 212 including a split ring 214 manually controlled by a lever 216 to selectively alternate between a first mode of operation and a second mode of operation. Again, the first mode of operation provides smooth movement of a guide wheel 40 relative to a housing 12 and the second mode of operation provides ratcheted movement of the guide wheel relative to the housing 12.

The guide wheel 40 is illustrated to include a central hub 218 of reduced diameter. The central hub 218 includes an outer diameter defining a first plurality of locking grooves or teeth 220. The split ring 214 is shown to be generally toroidal in shape and includes an inner diameter defining a second plurality of locking grooves or teeth 222 which cooperate with the first plurality of locking teeth 220. The split ring 214 is constructed of a resilient plastic material and is normally in a contracted state in which the plurality of teeth 220 and 222 are engaged and ratcheted movement of the guide wheel 40 relative to the housing 12 is provided. This condition of the split ring 214 is shown in solid lines in FIG. 14.

The split ring 214 defines an opening 224 which receives an end 226 of the lever 216. The opening 224 is generally oval in shape and the end 226 of the lever 216 is similarly shaped. When the lever 216 is in a first position (as shown) in FIG. 12 in solid lines, the end 226 of the lever 216 fits within the opening 224 of the split ring 214 without resiliently biasing the split ring 214 to an expanded condition. When the first mode of operation (e.g., smooth movement of the guide wheel 40 relative to the housing 12) is desired, the lever 216 is manually rotated either clockwise or counterclockwise about its pivot axis 230 to a second position (shown in FIG. 12 in broken lines). In this second position, the geometry of the end 226 of the lever 216 forces the split ring 214 from its contracted position to an expanded condition (shown in FIG. 14 in broken lines). As such, free movement of the guide wheel 40 relative to the housing 12 is permitted.

While the invention has been described in the specification and illustrated in the drawings with reference to a preferred embodiment, it will be understood by those skilled in the art that various changes may be made and equivalents may be substituted for elements thereof without departing from the scope of the invention as defined in the claims. In addition, many modifications may be made to adapt a particular situation or material to the teachings of the invention without departing from the essential scope thereof. Therefore, it is intended that the invention not be limited to the particular embodiment illustrated by the drawings and described in the specification as the best mode presently contemplated for carrying out this invention, but that the invention will include any embodiments falling within the description of the appended claims.

What is claimed is:

1. A steering mechanism for a catheter having a housing and a steering member, the steering mechanism comprising:
    a split locking ring normally biased to engage the steering member in a first mode to provide ratcheted movement of the steering member, and resiliently expandable to disengage from the steering member in a second mode to provide smooth movement of the steering member; and
    a lever operated cam carried by the housing and operative to resiliently expand the locking ring.

2. The steering mechanism of claim 1, wherein the steering member includes a first plurality of grooves, and the locking ring includes a second plurality of grooves for selectively engaging the first plurality of grooves.

3. The steering mechanism of claim 2, wherein each of the first and second plurality of grooves define teeth.

4. A steerable catheter comprising:
    a housing;
    an elongated tube extending from the housing;
    a steering member movably attached to the housing and interconnected to a distal tip of the elongated tube such that movement of the steering member cause a corresponding angular movement of the distal tip of the elongated tube; and
    a split locking ring normally biased to engage the steering member in a first mode to provide ratcheted movement of the steering member relative to the housing, and resiliently expandable to disengage from the steering member in a second mode to provide smooth movement of the steering member relative to the housing.

5. The steerable catheter of claim 4, further comprising a lever operated cam carried by the housing and operative to resiliently expand the locking ring.

6. The steerable catheter of claim 4, wherein the steering member includes a first plurality of grooves, and the locking ring includes a second plurality of grooves for selectively engaging the first plurality of grooves.

7. The steerable catheter of claim 6, wherein each of the first and second plurality of grooves define teeth.

* * * * *